(12) United States Patent
Wilson et al.

(10) Patent No.: US 7,635,000 B2
(45) Date of Patent: Dec. 22, 2009

(54) TRACHEAL TUBE ANTI-DISCONNECT DEVICE

(76) Inventors: Elouise Wilson, 2234 W. 19th Ave., Gary, IN (US) 46404; Linda M. Marino, 7505 Madison St., Merrillville, IN (US) 46410

( * ) Notice: Subject to any disclaimer, the term of this patent is extended or adjusted under 35 U.S.C. 154(b) by 432 days.

(21) Appl. No.: 11/316,548

(22) Filed: Dec. 22, 2005

(65) Prior Publication Data

US 2007/0144527 A1 Jun. 28, 2007

(51) Int. Cl.
*A61M 16/00* (2006.01)
(52) U.S. Cl. .............................. 128/207.17; 128/207.14
(58) Field of Classification Search ............ 128/207.15, 128/207.14, 207.17, 202.18, 206.12, 200.26, 128/200.24, 207.18; 604/174, 179, 181
See application file for complete search history.

(56) References Cited

U.S. PATENT DOCUMENTS

| | | | | |
|---|---|---|---|---|
| 3,640,273 A * | 2/1972 | Ray | | 602/5 |
| 4,331,144 A * | 5/1982 | Wapner | | 128/207.17 |
| 4,844,061 A * | 7/1989 | Carroll | | 128/207.17 |
| 5,101,822 A * | 4/1992 | Kimmel | | 128/207.14 |
| 5,251,616 A * | 10/1993 | Desch | | 128/200.26 |
| 5,282,463 A | 2/1994 | Hammersley | | 128/207.15 |
| 5,297,546 A * | 3/1994 | Spofford et al. | | 128/207.14 |
| 5,341,802 A | 8/1994 | Calegaugh | | 128/207.17 |
| 5,357,952 A | 10/1994 | Schuster et al. | | 128/207.17 |
| 5,362,303 A * | 11/1994 | Jasen et al. | | 602/17 |
| 5,368,024 A * | 11/1994 | Jones | | 128/207.17 |
| 5,490,504 A * | 2/1996 | Vrona et al. | | 128/207.17 |
| 5,529,062 A * | 6/1996 | Byrd | | 128/207.17 |
| 5,839,437 A | 11/1998 | Briggs, III | | 128/207.17 |
| 5,975,080 A | 11/1999 | Delaplane et al. | | 128/207.17 |
| 6,009,872 A | 1/2000 | Delaplane et al. | | 128/207.17 |
| 6,047,699 A | 4/2000 | Ryatt et al. | | 128/207.17 |
| 6,105,573 A | 8/2000 | Delaplane et al. | | 128/200.26 |
| 6,135,111 A * | 10/2000 | Mongeon | | 128/207.15 |
| 6,484,724 B1 * | 11/2002 | Sloan | | 128/207.17 |
| 6,612,309 B1 * | 9/2003 | Ancona | | 128/207.17 |
| 6,722,369 B1 | 4/2004 | Kron | | 128/207.17 |

* cited by examiner

*Primary Examiner*—Justine R Yu
*Assistant Examiner*—Arundipta Shome
(74) *Attorney, Agent, or Firm*—Thomas J. Schab

(57) ABSTRACT

An improved tracheal tube anti-disconnect device for securing a ventilator tube to an adapter that is connected to a tracheal tube. The device is comprised of a neck band that includes a pair of anchoring strips that releasably connect the neck band to a neck plate, an anti-disconnect fastening assembly that releasably secures to the neck band and which positively retains a ventilator circuit in communication with the tracheal tube. A retention system is provided on the neck band to prevent the anti-disconnect fastening assembly and the anchoring strips from disconnection with the neck band, thereby ensuring the communication between the ventilator circuit and the tracheal tube.

8 Claims, 4 Drawing Sheets

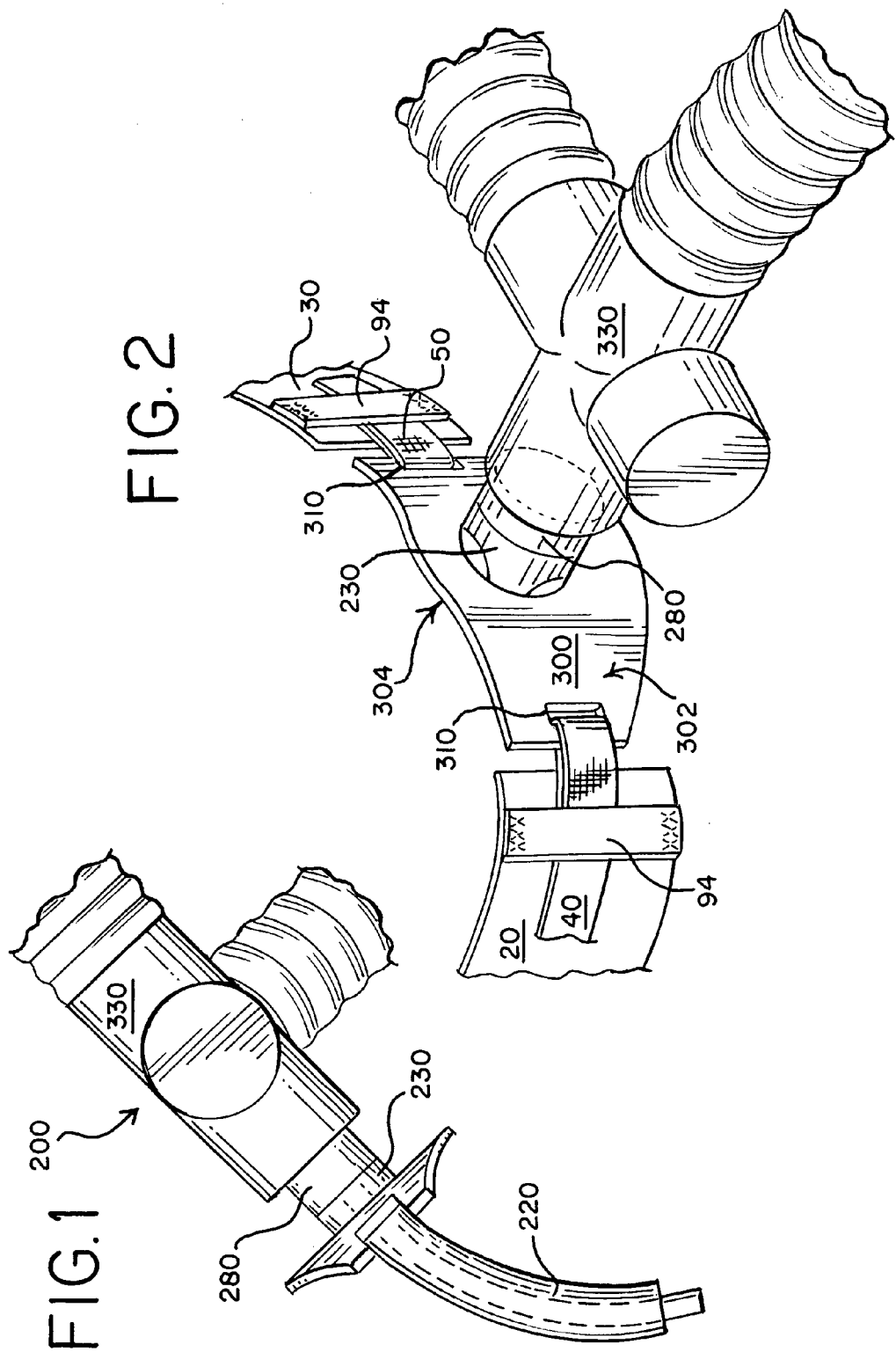

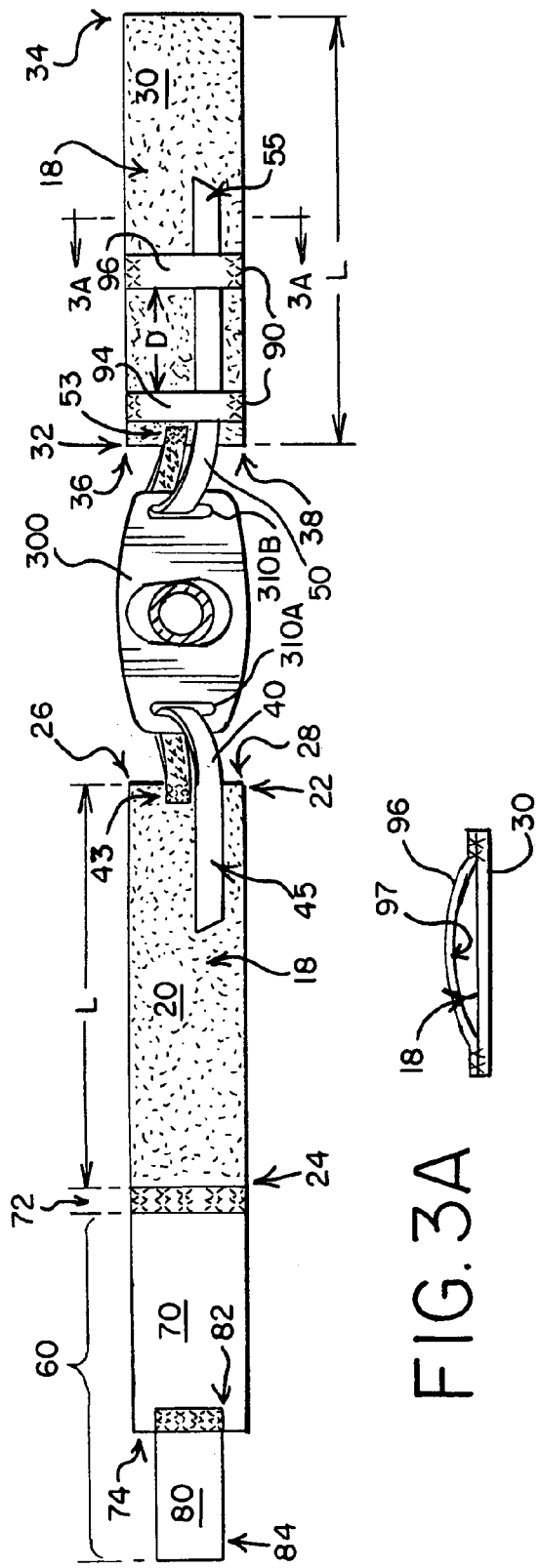

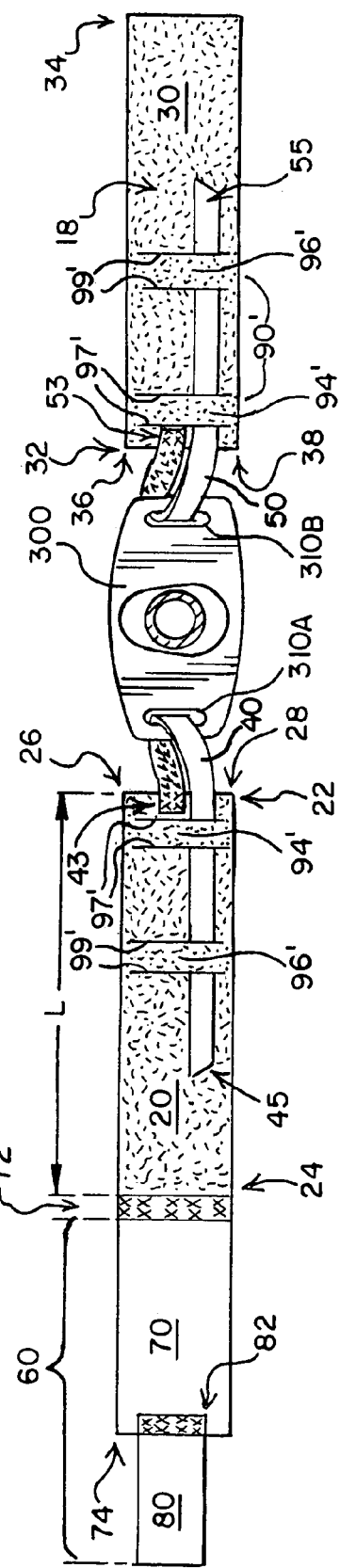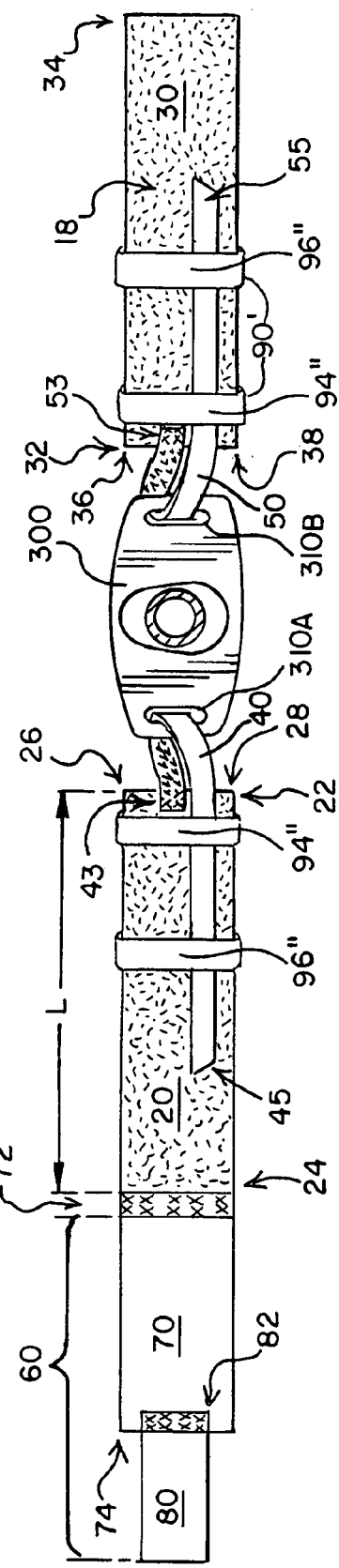

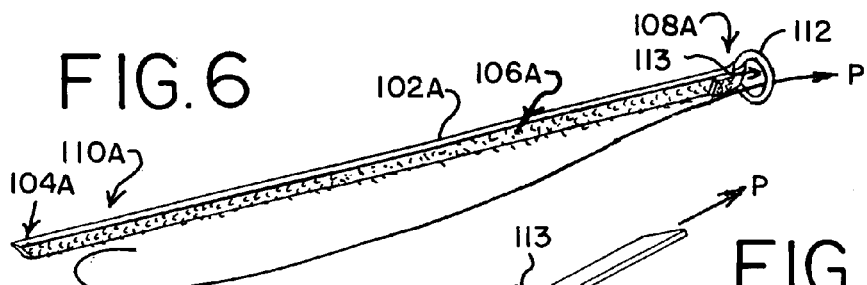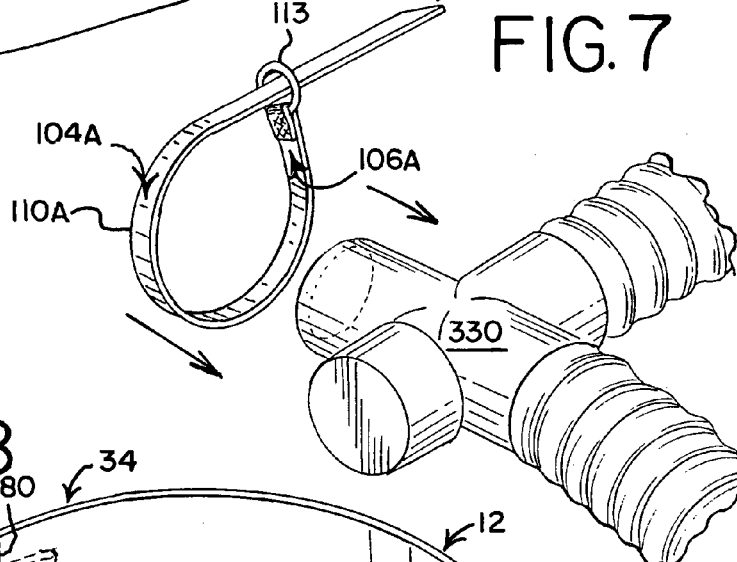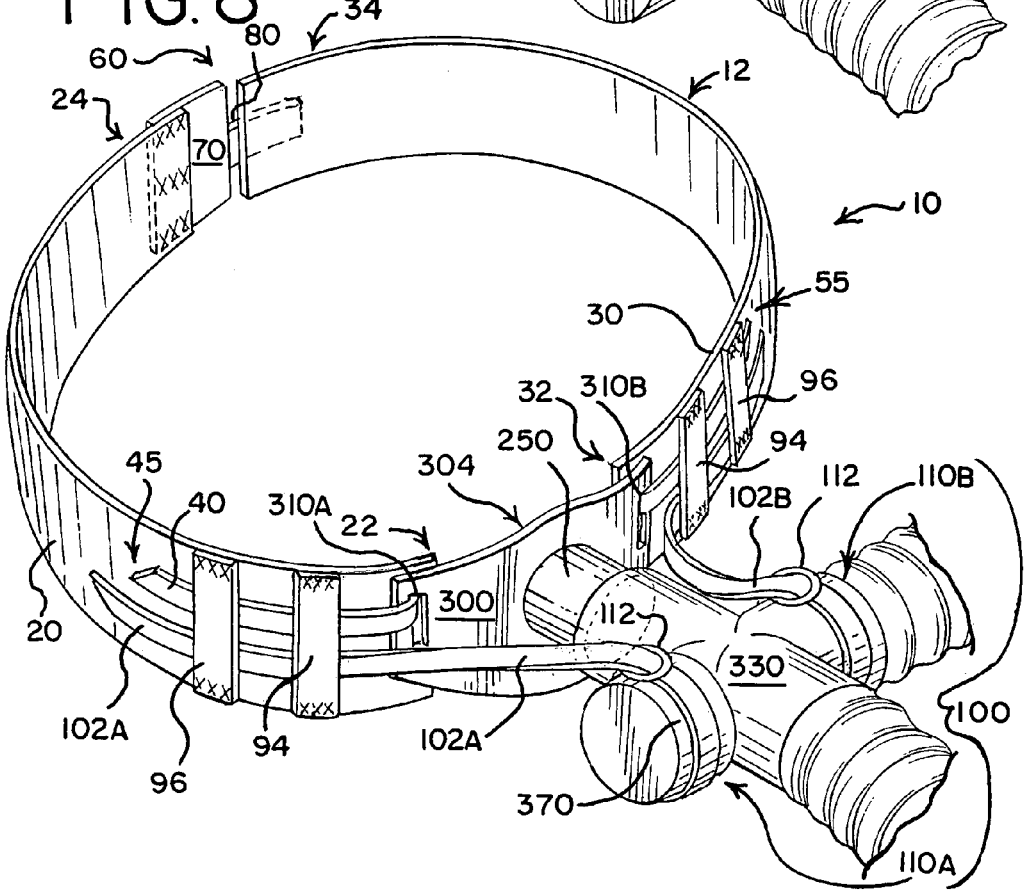

TRACHEAL TUBE ANTI-DISCONNECT DEVICE

BACKGROUND OF THE INVENTION

1. Field of the Invention

The present invention generally relates to a medical device for securing a tube to a patient, and more particularly to an improved type of anti-disconnect device that secures a tracheostomy or tracheal tube to a patient and for positively retaining a ventilator tube connector to the tube.

2. Discussion of the Prior Art

Tracheostomy and tracheal tubes are prevalently used in hospitals to assist a patient in breathing, where a tracheal tube is placed directly into the trachea or airway of a patient. A ventilator system is then connected to the tracheal tube to provide controlled ventilation. Conventional tracheal tubes consist of two portions. The first portion includes a tube-like part that is inserted directly into the airway of the patient and secured therein by a balloon inflation mechanism. The first part is known by those in the medical field as an outer cannula portion and it is usually pivotably connected to a neck plate which is designed to limit the lateral movement of the tracheal tube after its insertion within the trachea. The second portion is also tube-like and it slidably inserts within the first tubular part; this second portion is known by those in the medical field as the inner cannula portion. The inner cannula portion has one end that terminates with a universal connection piece that is cylindrically shaped. The medical industry refers to this piece as a universal connection because the outside and inside diameters of the connection piece are set to follow an industry standard so that the same fitting can be adapted to fittings provided by various manufacturers which eventually connect to the ventilator system. The universal connection piece has a set of tabs on one of its ends that allow it to snap fit onto one of the ends of the outer cannula. The other end of the universal connection piece attaches to an adapter through a friction fit. The most common type of adapter used in hospitals today is a T-shaped adapter although some hospitals may still use adapters which are shaped like a 90° elbow. The adapter, in turn, connects to the tubing that is associated with the ventilator machine.

One of the most prevalent problems with such tracheal tube and adapter arrangements is that patients are continuously moving or being moved throughout the day and even while they sleep, thereby causing the adapter to become either fully or partially dislodged from the tracheal tube. More specifically, the movement of the patient causes the friction fit connection between the universal connection piece and the adapter to fail and pull apart. In most instances, a total disconnection of the ventilation system from the adapter would present a life-threatening situation, however, the same may be true if the ventilator only becomes partially disconnected. Therefore, it is a priority that the integrity of the connection between the ventilator and the adapter be continuously maintained until the attending nurse or respiratory therapist purposely breaks the connection for various reasons.

Various types of prior art devices have been proposed to stabilize and/or prevent the tracheal tube from disconnection with the ventilator system. Still other prior art devices have attempted to provide an anti-disconnect between the neck plate and the adapter. For example, in U.S. Pat. No. 6,047,699 to Ryatt et al., an attachment body is designed to wrap around the body of the T-shaped adapter such that a pair of laterally spaced tabs are presented for insertion through slots formed in the opposed lateral flanges of the neck plate. The tabs are then folded back onto themselves and attached thereto through provision of hook and pile material on the appropriate sides of the tabs. This device has the shortfall of requiring the health care attendant to thread the tabs through the small slots of the neck plate while it is pressed tightly against the patient such that the attendant has to push or pull on the patient's neck and skin in order to slip the tabs around the backside of the neck plate. Such action creates unnecessary discomfort for the patient while being a very frustrating and time consuming endevor for the health care attendant. Furthermore, because the tabs are rather insubstantial in size, they easily become unhooked from themselves as the patient moves, thereby defeating the purpose of the device. Other prior art devices have also attempted to secure a form of an anti-disconnect device directly to the neck plate, as in U.S. Pat. No. 5,282,463 to Hammersley and U.S. Pat. Nos. 5,975,080, 6,009,872 and 6,105,573 to Delaplane et al. However, a common problem with each of those devices is that the anti-disconnect means, which attaches to the neck plate, slides off one of the lateral ends of the neck plate when the patient turns his head in a lateral direction. Still other prior art devices have employed hook and loop material strapping systems (Velcro®) to attach to the neck band that wraps around the neck of the patient for securing the neck plate thereto. The strap type of devices have been favored by heath care attendants because of their expediency and simplicity and examples of those types of devices can be found in U.S. Pat. No. 6,822,509 to Kron, and U.S. Pat. No. 5,839,457 to Briggs III and U.S. Pat. No. 5,357,952 to Schuster et al. Although these devices are much simpler, they all have the common problem of the straps disconnecting from the neck band during patient movement because there is no provision for restraining the straps against the neck band during patient movement. It should be appreciated that during patient movement, the tension on each of straps creates a tendency to pull the hook material off the loop material. Furthermore, the dimensional size of the straps does not provide enough contact area between the hook and loop material to continuously maintain the connection. Therefore, from the above discussion of prior art devices, it should be understood that most tracheal tube securing devices do not provide adequate means for stabilizing the position of the transverse portion of the adapter to prevent undesired rotation or other movement of the adapter as the patient moves, thus a partial or complete disassociation with the ventilator results.

Heretofore, the ability to retain the T-shaped and 90° elbow adapters in continuous connection with the universal connection piece has been highly limited. Ideally, it would be desirable to provide an improved tracheal anti-disconnect device that overcomes the deficiencies of the prior art devices by providing an anti-disconnect device that is comfortable to the patient, easy to apply and remove, and which maintains the integrity of the connection between the adapter and the universal connection piece.

SUMMARY OF THE INVENTION

It is a principal object of the present invention to provide an improved anti-disconnect device for use with an tracheal tube assemblage that comprises an outer cannula secured to a neck plate having a pair of opposed slots therein, an inner cannula having a first end inserted within said outer cannula and a second end that presents an universal connection piece, and an adapter connected to said universal connection piece and in communication therewith. The adapter of the tracheal tube assemblage is connected to an assisted breathing apparatus and in communication therewith. The object of the invention is met by providing an improved anti-disconnect device which comprises a flexible, resilient neck band having an elongated body comprised of identical first and second body halves, each half having corresponding first and second ends and corresponding front and back surfaces, wherein each of the front surfaces are comprised of a hook receiving type of material and each of the first ends have an anchoring means permanently attached thereto for releasably securing the neck plate between each of said first and second body halves of said neck band. The second ends of the neck band halves have a shared connections means for connecting both neck band halves to the patient. The anti-disconnect device further comprises an anti-disconnect fastening assembly adapted to stabilize and hold said adapter of said tracheal tube assemblage so as to prevent its dislogement from said universal connection piece. The anti-disconnect device further includes an anti-disconnect retention means for preventing said anti-disconnect fastening assembly and said anchoring strips from disconnection from said neck band during movement of said patient. Finally, the anti-disconnect device comprises a retention means provided on each of the neck band halves for retaining the anchoring means and the anti-disconnect fastening assembly against the neck band so as to prevent disconnection.

In another aspect of the invention, each of said anchoring strips has a pair of opposed ends and an interior and exterior surface, each of said exterior surfaces bearing a hook type of material and each of said interior surfaces bearing hook receiving type of material, wherein each of said anchoring strips is adapted for passage through a respective slot of said neck plate. In that same aspect of the invention, the anti-disconnect fastening assembly comprises at least one resilient, elongated fastening strap that engages said adapter and simultaneously attaches to said neck band.

The features and advantages of the invention will be further understood upon consideration of the following detailed description of an embodiment of the invention taken in conjunction with the drawings, in which:

BRIEF DESCRIPTION OF THE DRAWINGS

FIG. 1 is a side elevational view of a tracheal assemblage connected to a T-shaped adapter, which is connected to ventilator tubing;

FIG. 2 is a perspective view showing the tracheal assemblage connected to the neck band of the present invention;

FIG. 3 is a front elevational view of the neck band halves comprising the neck band of the present invention as attached to a neck plate, the right neck band showing the preferred embodiment of the anti-disconnect retention means of the invention attached thereto;

FIG. 3A is a side elevational view of the right neck band halve taken along line 3a-3a shown in FIG. 3;

FIG. 4 is a top elevational view of the neck band of the present invention shown in FIG. 3;

FIG. 5A is a front elevational view of the neck band halves comprising the neck band of the present invention attached to a neck plate, the right neck band showing a second embodiment of the anti-disconnect retention means being formed therein;

FIG. 5B is a front elevational view of the neck band halves comprising the neck band of the present invention attached to a neck plate, the right neck band halve showing a third embodiment of the anti-disconnect retention means being secured thereabout;

FIG. 6 is a perspective view showing a fastening strap of the anti-disconnect fastening assembly of the present invention;

FIG. 7 is an exploded perspective view showing the fastening strap of FIG. 6 in a pre-assembled relation about a T-shaped adapter having ventilator tubing attached thereto; and FIG. 8 is a perspective view of the present invention showing the anti-disconnect fastening assembly attached about the T-shaped adapter and being prevented from disconnection from the neck band by the anti-disconnect retention means attached to the neck band, the view further showing the anchoring means securing the neck plate to the neck band, with the anchoring means being prevented from disconnection from the neck band by the anti-disconnect retention means.

DETAILED DESCRIPTION OF A PREFERRED EMBODIMENT

Referring to FIGS. 1 and 2, a tracheostomy tube assemblage 200 includes an elongated, curved outer cannula portion 220 terminating at an enlarged head section 230. The head section is provided with an internal socket (not shown) which defines an inside diameter. The socket is in communication with the outer cannula portion 220. The enlarged head section 230 is connected to a neck plate 300 through either a pivotal or fixed connection and the outer cannula portion 220 is held within the trachea of the patient by provision of a small balloon device (not shown). Inserted within the socket of the head section 230 and passed down the outer cannula portion 220 is the inner cannula portion 240, shown in dashed line form in FIG. 1. One end of the inner cannula portion 240 is provided with the cylindrically shaped universal connection piece 280, which interlocks within the socket of the enlarged head section 230. FIGS. 1 and 2 show the universal piece 280 being interlocked to the enlarged head section 230. The universal connection piece 280 has an outside diameter that made to be an industry standard of 22 millimeters. In this way, the various makers of ventilator systems will always be able to fit their particular systems to the standard universal connection piece 280 without the need for additional connector pieces. The neck plate 300 has a pair of opposed and identical slots 310 that extend between front surface 302 and rear surface 304. In operation, the rear surface 304 will be in contact with the patient's neck, as will become clearer later herein.

Referring now to FIGS. 3-6, the preferred embodiment of an tracheal tube anti-disconnect device according to the present invention is shown at 10. A first component of the anti-disconnect device is comprised of a neck band which is shown in detail in FIGS. 3 and 4. The neck band has an elongated body 12 made from a central sponge-like, foam layer 14 joined between two outside layers 16,18. The neck band 12 is both flexible and resilient wherein the interior layer 16 defines an interior surface made from a cotton fiber that will contact the patient's skin so as to prevent irritation, while the exterior layer 18 defines an exterior surface that is made from a loop or hook receiving type of material that forms part of the well-known material known under the tredemark VELCRO®. Each of the layers comprising the neck band are joined together by conventional means such as heat staking, gluing or stitching. As FIGS. 3 and 4 illustrate, neck band 12 is not a continuous band, but rather is comprised of two halves 20 and 30. Each neck band half 20,30 proper has a respective and corresponding first and second end 22,32 and 24,34, which define the longitudinal extent "L" of the band halves and a top and bottom edge 26,36 and 28,38, which define the vertical extent "V." The respective longitudinal and vertical extents of each band half are identical. Each of the first ends 22,32 has a respective and identical anchoring means 40,50 in the form of a resilient strip made of plastic or the like permanently attached by sewing to the respective neck band half. The second ends 24,34 are joined together behind a patient's neck through provision of a quick-release connection means 60. In FIGS. 3 and 4, the connection means 60 is shown attached to neck band halve 20 although it may be attached to either of the neck band halves 20,30. In a preferred embodiment, the connection means 60 comprises a releasable flap that is attachable to exterior layer 18 on neck band halve 30. The releasable flap is comprised of the combination of an elastic portion 70 and a plastic portion 80. The elastic portion 70 is comprised of an elastic band that has a first end 72 that is permanently attached by sewing to end 24 of neck band halve 20. A second end 74 of the elastic portion 70 is attached to the plastic portion 80 by sewing it to a first end 82 thereof. The plastic portion 80 has a smooth side 86 and a rough side 88 that is comprised of hook type of material. The hook type of material is complementary to the loop type material of exterior layer 18 so that second end 84 of the plastic portion 80 may be releasably connected and disconnected in an expeditious manner from exterior layer 18 on neck band halve 30. By incorporating the elastic portion 70, the overall length of neck band 12 can be stretched so as to provide adjustment for patients having a larger diameter neck. Although the preferred embodiment of the connection means 60 employs a hook and loop connection, it is envisioned that other means for establishing this connection may be employed. For example, the connection means could comprise buckles, snaps, buttons, or even simple tying mechanisms, etc. Furthermore, it is also anticipated that in another embodiment of the invention, the connection means 60 does not include the elatistic portion 70, so that plastic portion 80 has its first end 82 directly stitched to either of the band half ends 24,34.

As mentioned above, because the anchoring means 40 and 50 are identical, only the anchoring means 40 will be described in greater detail although it should be understood that all aspects of the construction, attachment to the neck band half, and function of each anchoring means will be the same regardless of which neck band halve is being described. As FIGS. 3 and 4 show, anchoring means 40 is comprised of the resilient anchoring strip that is defined by a pair of opposed ends 43 and 45, and an interior surface 47 and an exterior surface 49. The exterior surface 49 is made of a hook type of material that is complementary to the loop type material of exterior layer 18, while first end 43 is permanently attached to exterior layer 18 by sewing. Alternatively, anchoring strip 40 could be attached to the interior layer 16. However, it has been discovered that when it is attached to that side of the neck band, the strip occasionally becomes twisted during use, thereby causing the hook material to directly contact and rub against the patient's skin, leading to scratching and irritation of the skin. Therefore, it is preferable to attach anchoring strip 40 to the exterior layer 18 of neck band 12 because if the strip becomes twisted during attachment, the hook material will always contact against the neck band itself, rather than facing and contacting against the patent's skin. The free or second end 45 of anchoring strip 40 is adapted to be passed through one of the opposed slots, in this case slot 310A, in the neck plate 300, and then doubled back along exterior layer 18 for releasable securement to the neck band havle 30 in a longitudinal direction, as shown in FIGS. 3 and 4. Those in art know that although there are several different types of neck plate manufacturers, all of the various types of neck plates 300 essentially function in the same manner where the endotracheostomy tube assemblage 200 is held stationery with respect to the center of the plate and that all of the plates present an opposed set of slots 310A,310B. Therefore, it should be apparent that it is an advantage that the neck band of the present invention can be attached to any one of the manufacturer's neck plates. In accordance with the invention, the anchoring strips 40 and 50 further provide an expeditious and efficient manner in which to firmly and securely hold the tracheal tube assemblage in a set position without any part of the anchoring means slipping off the lateral ends of the neck plate 300 as the patient moves his head, which is very typical of the device presented in U.S. Pat. No. 6,105,573 and the like.

FIGS. 3 and 4 best illustrate that the present invention is seen to also include the anti-disconnect retention means shown at 90. In both FIGS. 3 and 4, the anti-disconnect retention means 90 is only shown on neck band halve 30 for the sake of clarity, although it should be understood that neck band halve 20 will include identical retention means 90 at a corresponding location. A common problem with prior art anti-disconnect devices is that they become disconnected from the neck band with patient movement. The primary function of the anti-disconnect retention means 90 of the present invention is to positively retain an anti-disconnect fastening assembly 100, also a part of the present invention, from disconnection with the neck band. The anti-disconnect fastening assembly 100 will be explained below. A secondary function of the anti-disconnect retention means 90 is to positively retain the anchoring means 40,50 from disconnection with the neck band. Because the retention means 90 on each neck band halve 20 and 30 are identical, only retention means 90 on neck band halve 30 will be described in greater detail. As FIG. 3 shows, the retention means 90 comprises at least one, but preferably at least two, horizontally disposed and longitudinally displaced loops 94 and 96 that are permanently attached to exterior layer 18 by sewing. The first loop 94 is positioned near the first end 32 of neck band halve 30. Its has been experimentally found that the best location for the first loop 94 on the neck band halve is about a half inch (0.50 inches) from each end (32) so that when the two neck band halves 20,30 are connected to the neck plate 300, the first loop 94 on each neck band half will be juxtapositioned with the lateral ends of the neck plate 300. It is a provision of the present invention to ensure that at least some of the neck band half 20 is interposed between the neck of the patient and the rear surface 304 of the neck plate 300 so that the neck plate does not directly contact the skin and cause prolonged, pressure against the skin. Prolonged pressure against the skin will eventually lead to edema. To avoid this serious problem, it is seen in FIG. 6, that about one half inch (0.5 inch) of each of the first ends 22,32 of the neck band halves 20,30 are positioned underneath the bottom surface 302 of neck plate 300 so as to prevent the opposed ends of neck plate 300 from contacting the patient. Therefore, it is preferred that after the neck band is attached about the patient's neck, that the first loop 94 on each neck band half be disposed in a juxtapositioned position with each lateral end of the neck plate, regardless of which manufacturer's neck plate is used. The second loop 96 is longitudinally displaced from the first loop 94 by a predetermined distance "D." In practice the present invention has been found to best function when "D" is at least one inch (1.0 inch), but no more than one and one half inches (1.5 inches), which is the preferred distance "D." As long as the distance "D" is at least one inch, a nurse or a respiratory therapist will be able to readily secure and remove any type of strip that will be retained to exterior surface 18 of neck band 12. It is also important to ensure the proper function of the rention means 90 by providing a gap between the inside surface of each respective loop 94,96 and the exterior surface 18. This point is exemplified in FIG. 3A, where a gap is seen to exist between inside surface 97 of loop 96 and exterior surface 18. If this gap is too large, there will be an opportunity for the strips of anchoring means and the straps of the anti-disconnect fastening assembly to disconnect from from the neck band 12, thus defeating the purpose of the retention means 90. Therefore, it is preferable that the gap be no more than the thickness of a pencil, which is about a fourth of an inch (0.25 inch) If the spacing is less than the width of a pencil, the insertion and removal of the anchoring means and fastening assembly straps within the retention means by the health care provider will become unreasonably difficult, if not impossible, especially since the insertion and removal occurs while the neck band is in place on the patient. It is also preferred that each loop be constructed from an inelastic, very durable material such as a cotton weaving in order to prevent the loops from stretching, as each loop will undergo continuous tension from the anchoring means 40,50 and from the anti-disconnect fastening assembly 100, as the invention is put into practice, as will be explained shortly herein. In order to overcome the difficulty that the heath care provider might encounter when inserting and removing any form of strap or strip from within the retention means, it is also preferred that the free ends of the strips and/or straps be provided with a sealed end so that the hook material on the respective ends does not attach to the hook receiving material on the exterior surface of the neck band as they are passed underneath the individual loops.

Another embodiment of the anti-disconnect retention means 90' is shown in FIG. 5A, where it is seen that instead of structural loops being permanently attached to the exterior surface 18 of each neck band half 20,30, the loops 94' and 96' are formed as integral parts of the neck band halves. The anti-disconnect means 90' is formed by the provision of two sets of vertically oriented slits 97' and 99' in each of the neck band halves. Each set of slits 97' and 99' allows the neck band material between the slits to be pulled away from the material of the neck band proper, to form the two respective sets of loops 94' and 96'. Each set of loops function exactly as the loops 94,96 and is displaced from each other as set forth earlier.

A third embodiment of the anti-disconnect means 90" is shown in FIG. 5B, where the loops 94" and 96" are not permanently attached to the neck band halves, but rather are separate elements 97" and 99" that wrap around the body of the neck band halves so as to hold the anti-disconnect fastening means 100A,100B and the anchoring means 40,50 against the neck band. The external loops 94" and 96" can be formed of straps that have snaps, buckles or Velcro means on them so as to perform the same function in that they would be applied to the neck band after the anchoring strips and the fastening straps are attached to the neck band, thereby preventing them from disconnection with the neck band.

Now referring to FIGS. 6-8, the present invention is seen to further comprise the anti-disconnect fastening assembly 100. As best seen in FIG. 8, the fastening assembly 100 is seen to comprise in combination, a pair of flexible, resilient, elongated fastening straps 102A,102B that functionally stabilize and hold the T-shaped adapter 330 and prevent it from becoming dislodged from the universal connection piece 250. Each fastening strap 102A,102B is preferrably constructed of a plastic or the like and each is identical to the other. Only fastening strap 102A will be shown and described in FIGS. 6 and 7. Each strap will have a corresponding bottom surface 104A,104B and a corresponding top surface 106A,106B. Each top surface 106A,106B presents a hook type of material, while each bottom surface 104A,104B presents a relatively smooth surface. Each fastening strap 102A,102B also has a corresponding first end 108A,108B that includes a geometrically shaped ring 112 permanently attached thereto, wherein the pheripheral shape of the ring defines a central opening 113. A corresponding second end 110A,110B of each fastening strap is considered to be the free end, whereby each respective free end 110A,110B is inserted back through each respective central opening 113 in the direction of the heavy arrow P, and then pulled tauntly so that each fastening strap 102A,102B is tightly engaged about the cross member ends 370A and 370B of the T-shaped adapter 330. Once secured tightly about the T-shaped adapter 330, each respective free end 110A,110B of the anti-disconnect fastening assembly 100 is secured to the exterior surface 18 of neck band 12 by passing each free end under the respective loop sets 94,96 of the anti-disconnect retention means 90. Of course, when each of the fastening straps 102A,102B are wrapped around the adapter 330, it is desired that the respective bottom surfaces 106A,106B, which have the hook type of material, contact the exterior surface of the adapter cross member ends 370A, 370B. In this way, the hook type of material will be contigious with the hook receiving type of material of the exterior surface 18 of neck band 12 for releasable securement to a respective neck band halve 20 and 30. If the fastening straps 102A and 102B were wrapped around the cross member ends 370A and 370B such that the top surfaces 104A and 104B were in contact with the outer surface of the cross member, then the hook type of material of the bottom surfaces 106A,106B, would be exposed to the skin under the patient's chin, possibly leading to scratching and chaffing of that area as the patient moves his head in an upward and downward direction. Should the health care provider discover that she has wrapped the fastening straps 102A,102B around the adapter with the hook material exposed, she can either twist each of fastening straps so that the hook material faces away from the patient's skin prior to fastening them to the neck band 12, or simply and expediently remove and re-wrap the fastening straps.

Referring to FIG. 8, the operation of the anti-disconnect device 100 of the present invention proceeds as follows. First, each of the first ends 22,32 of each respective neck band half 20,30 are positioned underneath the lateral flanges of the neck plate 300 such that a small portion of the respective neck band half will be interposed between the bottom surface 304 of the neck plate 300 and the patient. Then the free ends 45,55 of each anchoring strip 40,50 are threaded through the respective neck plate slots 310A,310B. The respective free ends 45,55 are then folded back for insertion through the respective first loops 94 of the anti-disconnect retention means 90, and then threaded through the respective second loops 96, as best seen in FIG. 3. The hook material on the respective exterior surfaces of each anchoring strip 40,50, is then tightly pressed against the loop material (hook receiving material) comprising the exterior layer 18 of each neck band halve 20,30. In practice, the anchoring strips 40,50 can be located anywhere along the vertical extent "V" of the neck band half as long as the exterior surface 18 presents an adequate amount of free surface area for the anchoring strips 102A,102B to be secured to that surface too. That point is understood when viewing FIG. 8, where it is seen that the anchoring strips 40,50 are secured to exterior surface 18 above the fastening straps 102A, 102B. After securing the anchoring strips, the second ends 24,34, of the neck band halves 20,30, are then releasably secured about the neck of the patient by utilization of the connection means 60. The rough side 88 of plastic portion 80 presents the hook type of material for releasable connection to the exterior surface 18. Should the patient have an extraordinarily large neck, the elastic portion 70 will stretch and accommodate the patient without placing an undue amount of tension on the neck surface. If an elastic portion 70 is not provided as a component of the connection means 60, then the plastic portion 80 will be directly fastened to the exterior surface 18 on an opposing neck band half. After securing the neck plate 300 to the neck band 12, the tracheal tube assemblage 200 is then connected together, as is well known by those in the art. Finally, the anti-disconnect fastening assembly 100 is employed so as to stabilize and hold the T-shaped adapter 330 to the universal connection piece 250. In particular, each of the anchoring straps 102A,102B of the anti-disconnect fastening assembly 100 are respectively wrapped around the outer surface of the cross member ends 370A, 370B of the T-shaped adapter 330, whereby the respective second and free ends 110A,110B, are inserted through the central opening 113 of each respective ring 112 and then pulled tightly so that the respective straps 102A,102B are wrapped tauntly about the T-shaped adapter 330. The hook material on the bottom surfaces 106A,106B should be in contact with the outer surface of the cross member ends 370A and 370B. If the adapter is not T-shaped, but rather is an elbow shaped adapter, then only one of the fastening straps of the anti-disconnect fastening assembly would be used and it would be wrapped about the exterior surface of the adapter. Those in the art are familiar with an elbow shaped adapter in that they are shaped exactly like the 90° elbow that is used in plumbing and understand that those older styles of adapters are hardly ever used, therefore, it has not been shown in the drawing figures.

FIG. 8 also shows that after securing each respective anchoring strap 102A,102B is wrapped about the cross member ends 370A,370B, the free ends 110A,110B of each respective strap 102A,102B are then threaded through the respective anti-disconnect rention means 90 on each neck band half 20,30. The free ends 110A,110B are inserted through the respective first loops 94 and then through the respective second loops 96 before each anchoring strap 102A, 102B is pressed against the respective neck band halve 20,30. The hook material on each anchoring strap releasably engages the loop or hook receiving type of material of the exterior layer 18 of each neck band halve. In operation, no matter how often or in what direction the patient moves his head, the retention means 90 functions to direct and maintain the anchoring straps 102A, 102B and the fastening strips 40,50, for that matter, in a tightly-held position against a substantial portion of exterior layer 18 of the neck band 12. As mentioned earlier, prior art problem anti-disconnect devices became easily disconnected from the neck band because there was no provision for holding prior art devices against the neck band, thereby limiting the contact surface area between the mating hook material and loop material. With the prior art, as the patient moved his head, the tension on the anti-disconnect straps would cause the straps to slowly pull themselves off the surface of the neck band, eventually leading to the anti-disconnect straps to either loosen badly, or completely disconnect. In that situation, further movement of the patient eventually would lead to the disconnection of the T-shaped adapter from the universal connection piece, thereby either fully or partially cutting off the air supply to the patient. The present invention ensures that the integrity of the anti-disconnect fastening assembly is continuously maintained, and for that matter, the integrity of the anchoring means too, thereby eliminating the occurrences of the patient disconnecting from the ventilator circuitry.

Furthermore, with the tracheal anti-disconnect device according to the present invention, an improved device is provided where health care personnel can expediently remove and reattach the T-shaped adapter for cleaning, providing respiratory care, or for complete replacement or cleaning of the inner cannula, while ensuring that the entire tracheal system is positively secured together independent of patient movement. While the apparatus herein disclosed forms a preferred embodiment of this invention, it will be understood that this invention is not so limited, and changes can be made without departing from the scope and spirit of this invention, which is defined in the appended claims.

We claim:

1. In a tracheal tube assemblage comprising an outer cannula secured to a neck plate having a pair of opposed slots therein, an inner cannula having a first end inserted within said outer cannula and a second end that presents an universal connection piece, an adapter connected to said universal connection piece and in communication therewith, said adapter of said tracheal tube assemblage connected to an assisted breathing apparatus and in communication therewith, an improved anti-disconnect device for securing said adapter to said universal connection piece, said device comprising: a flexible, resilient neck band having an elongated body, said neck band comprised of identical, disconnectable first and second body halves, each half having a corresponding top and bottom edge, a first and second end, and a corresponding front and back surface, each of said front surfaces comprised of a hook receiving type of material, each of said first ends having an anchoring means permanently attached thereto, each of said second ends having a shared, quick-release connection means for connecting said neck band to said patient, each of said anchoring means comprised of an identical anchoring strip for releasably securing said neck plate between each of said first and second body halves of said neck band, wherein each of said anchoring strips has a pair of opposed ends and an interior and exterior surface, each of said exterior surfaces bearing a hook type of material and each of said interior surfaces bearing hook receiving type of material, wherein each of said anchoring strips is adapted for passage through a respective slot of said neck plate;

an unfixed anti-disconnect fastening assembly adapted to stabilize and hold said adapter of said tracheal tube assemblage so as to prevent its dislodgment from said universal connection piece, said anti-disconnect fastening assembly comprised of at least one resilient, elongated fastening strap releasably connected to said neck band, said at least one fastening strap having a first end, a second and free end, a top side and a bottom side, said top side comprised of a hook type of material that mates with said hook receiving material of said neck band, said first end having a geometrically shaped ring attached thereto, said ring having a peripheral configuration that defines a central opening, said free end of said strap adapted to wrap about said adapter and insert through said central opening such that pulling said free end towards said patient causes said at least one fastening strap to incrementally tighten about said adapter wherein cooperation between said ring and said fastening strap maintains the tight engagement of said fastening strap about said adapter and wherein said free end of said fastening strap is further adapted to simultaneously attach to said neck band as it is engaged about said adapter, wherein said neck band further includes an anti-disconnect retention means associated with each of said neck band halves for preventing said anti-disconnect fastening assembly and said anchoring strips from disconnection from said neck band during movement of said patient, each of said anti-disconnect retention means comprised of at least two identical loops, each having an inside surface and an outside surface, and each made of an inelastic and durable material that extends between said top and bottom edges of said respective neck band half and which permanently attaches attached thereto at corresponding locations on said exterior surfaces near a respective said first end of said neck band half such that said first loop on each neck band half is positioned immediately adjacent to a respective neck plate slot when said neck band is secured to said patient and wherein said respective second loops are displaced a predetermined distance from said first loops, said predetermined distance being at least one inch (1.0 inch) and no greater than one and one half inches (1.5 inches) and wherein an identical and predetermined spacing exists between a respective inside surface of all loops and said exterior surface of said neck band half on which said loop is attached.

2. The anti-disconnect device of claim 1, wherein said connection means comprises a flap having hook means that releasably attaches to said exterior surface of said neck band.

3. The anti-disconnect device of claim 2, wherein said releasable flap is comprised of an elastic portion and a plastic portion, each portion having a first end and a second end, said first end of said elastic portion permanently attached to one of said second ends of one of said neck band halves and said first end of said plastic portion attached to said second end of said elastic portion.

4. The anti-disconnect device of claim 3, wherein said plastic portion has a smooth side and a rough side, said rough side comprised of a hook type of material that releasably attaches to said exterior surface of the other of said neck band halves.

5. The anti-disconnect device of claim 2, wherein said releasable flap is comprised of a plastic portion having a first end permanently attached to one of said second ends of said neck band halves, said releasable flap having a smooth side and a rough side wherein said rough side comprises a hook type of material that releasably attaches to said exterior surface of the other of said neck band halves.

6. The anti-disconnect device of claim 1, wherein said connection means is comprised of one of a snap means, button means, tying means and buckle means.

7. The anti-disconnect device of claim 1, wherein said predetermined spacing is such that a pencil will fit within said loop while simultaneously touching said inside surface of said loop and said exterior surface of said neck band half.

8. The anti-disconnect device of claim 1, wherein each of said loops is comprised of a material made from a cotton weaving.

* * * * *